United States Patent [19]

Liao et al.

[11] Patent Number: 5,437,997

[45] Date of Patent: Aug. 1, 1995

[54] **CAROTENOID PRODUCING CULTURE USING *NESPONGIOCOCCUM EXCENTRICUM***

[75] Inventors: Hans H. Liao, Madison, Wis.; Richard D. Medwid, Fort Collins, Colo.; Donald L. Heefner, Longmont, Colo.; Kathleen S. Sniff, Arvada, Colo.; Randal A. Hassler, Lafayette, Colo.; Michael J. Yarus, Boulder, Colo.

[73] Assignee: Universal Foods Corporation, Milwaukee, Wis.

[21] Appl. No.: 474,248

[22] Filed: Feb. 5, 1990

Related U.S. Application Data

[63] Continuation of Ser. No. 58,512, Jun. 5, 1987, abandoned.

[51] Int. Cl.$^6$ ............... C12N 1/12; C12N 1/00; A01H 13/00
[52] U.S. Cl. ................. 435/257.1; 47/1.4; 435/243
[58] Field of Search ............ 435/257, 243, 172.1; 47/1.4

[56] References Cited

U.S. PATENT DOCUMENTS

| | | | |
|---|---|---|---|
| 2,949,700 | 8/1960 | Kathrein | 47/58 |
| 2,974,044 | 3/1961 | Farrow | 99/4 |
| 3,108,402 | 10/1963 | Kathrein | 47/58 |
| 3,280,502 | 10/1966 | Farrow | 47/1.4 |

OTHER PUBLICATIONS

Ben-Amotz et al (1983) Ann. Rev. Microbiol. 37:95-119, p. 112 in particular.

M. R. Droap (1969) in J. R. Norris et al. eds., Methods in Microbiology, 3B, Academic Press, N.Y., pp. 286-299.

Vaisberg et al. (1976) Plant Physiol. 57(2):260-9, abstract cited.

H. C. Bold (1967) Morphology of Plants, Harper and Row, Inc., New York, p. 39.

Spurgeon, et al. "The Biochemistry of Plants" Chapter 14 (1980).

Marusich, et al., "Oxycarotenoids in Poultry Pigmentation" Poultry Sci. 49(6), pp. 1555-1566 (1970).

Urbach, et al. "Effect of Substituted Pyridazione Herbacides and of Difunone (EMD-IT 5914) On Carotenoids Biosynthesis in Green Algae" 31cZ. Naturforsch. pp. 652-655 (1976).

Van Nostrand's Schientific Encyclopedia, 80 (6th Ed. 1983).

Deason, "The Genera Spongiococcum and Neospongiococcum I. The Genus Neospongiococcum and the Multi-Nucliate Species of the Genus Neospongiococcum" Phycologia 10(1) (1971).

Deason, "The Genera Spongiococcum and Neospongiococcum. II. Species of Neospongiococcum With Labile Walls", Phycologia 10(2-3) (1971).

Deason, "The Genera Spongiococcum and Neospongiococcum (Chlorophycea, Chlorococcales) III, New Species, Biochemical Characteristics and A Summary Key", Phycologia 15(2) (1976).

Deason, "Taxonomic Significance of Secondary Carotenoid Formation in Neospongiococcum" J. Phycol. 13, pp. 176-180 (1977).

Deason, "Mitosis and Cleavage During Zoosporogenesis in Several Coccoid Green Algae", J. Phycol. 15, pp. 371-378 (1979).

Parker, et al. "Facultative Heterotrophy in Some Chlorococcasean Algae" Science 133, pp. 761-763 (1961).

(List continued on next page.)

Primary Examiner—Douglas W. Robinson
Assistant Examiner—Deborah K. Ware
Attorney, Agent, or Firm—Whyte Hirschboeck Dudek

[57] ABSTRACT

A culture for the production of xanthophylls comprising *Nespongiococcum excentricum* ATCC 40335 and mutants thereof. The culture having a dry cell weight xanthophyll content of at least about 0.65% and being capable of growing to a cell density of greater than about 40 grams per liter. The culture also comprising: carbon, phosphate, sulfate, iron, magnesium, and nitrogen.

4 Claims, 4 Drawing Sheets

OTHER PUBLICATIONS

Khadke, et al. "The Physiology of *Neospongiococcum Ovatum* Deason" New Phytol. 77, pp. 635–639 (1976).

Sylvester, et al. "Dark and Light Grown Algal Species of the Genus Neospongiococcum" Proceedings of the Pennsylvania Academy of Science vol. 49, Issue 2 (1975).

"Carotenoids and Related Compounds" pp. 53–83.

"Algae-Drived Xanthophylls for Pigmentation Control" Feeds Illustrated Nov. 1962.

Marusich, "Zeaxanthin as a Broiler Pigmenter" Poultry Science 55: 1486–94 (1976).

Kuzmicky, et al. "Pigmentation Potency of Zanthophyll Sources".

CRC Handbook of Microalgal Mass Culture pp. 339–419 (A. Richmond ed. 1986).

Theirault, *Heterotrophic Growth and Production of Xanthophylls by Chlorella Pyrenoidosa,* App. Microbiol. 13(3) pp. 402–416 (1965).

HSI (26,000X)

WILD TYPE (38,000X)

B14 (40,000X)

OFY 8 (40,000X)

CAROTENOID PRODUCING CULTURE USING *NESPONGIOCOCCUM EXCENTRICUM*

This is a continuation of application Ser. No. 07/058,512 filed on Jun. 5, 1987, now abandoned.

FIELD OF THE INVENTION

The present invention relates to methods for selecting photosynthetic microorganisms having increased levels of carotenoids. The invention is further directed toward microorganisms selected by such processes and, in particular, to a strain of the alga *Neospongiococcum excentricum* having increased levels of carotenoids and methods for fermentation of the microorganisms.

BACKGROUND

Carotenoids are accessory pigments in photosynthetic microorganisms which function by absorbing light and transferring energy to chlorophyll for photosynthesis. Carotenoid also acts to protect cells from photooxidative damage from oxygen radicals produced during photosynthesis. See generally Spurgeon, et al., *The Biochemistry of Plants*, Chap. 14 (1980).

Xanthophylls are oxygen-containing carotenoids and are useful as natural coloring agents. Xanthophylls and, in particular, lutein and zeaxanthin, are used as feed supplements for poultry to produce a yellowish color in shanks and egg yolks.

Production of carotenoids by fermentation of microorganisms is known. Farrow, U.S. Pat. No. 3,280,502 (1966), a process for the preparation of lutein is disclosed in which a strain of *Chlorella pyrenoidosa* is fermented and up to 235 mg of lutein per liter is produced in ninety-six hours. Kathrein, U.S. Pat. No. 2,949,700 (1960) discloses a process for the production of carotenoids by the cultivation of algae of the phyla Chlorophyta, including species of Chlorococcum, Chlorella, and Chlamydomonas. Microbiological production of carotenoids by fungi is also known. For example, see Farrow, U.S. Pat. No. 2,974,044 (1961).

The unicellular green alga *Nospongiococcum excentricum* produces xanthophylls and has been used as a feed additive to provide color. See, for example, Marusich, et al., *Oxycarotenoids in Poultry Pigmentation*, Poultry Sci. 49 (6) pp. 1555–1566 (1970).

While *N. excentricum* and other algae are known for producing carotenoids, known developed and wild type strains of algae do not produce sufficient levels of carotenoids for successful commercial production. Accordingly, there is a need for strains of algae having increased levels of carotenoids and methods for selecting such strains. Additionally, there is a need for methods of fermentation of algae for producing increased yields of carotenoids.

SUMMARY

The present invention is directed to a method for selecting photosynthetic microorganisms having increased cellular carotenoid content. A starting population of photosynthethic microorganisms is mutated. A mutated microorganism is then selected from the mutated population. The selected microorganism has a cellular chlorophyll content above a selection point. More particularly, the method of selection involves determining a chlorophyll content distribution in the mutated population. A selection point is then determined so that less than about 5.0% of the mutated population has a chlorophyll content above the selection point.

In one embodiment of the invention, the step of selecting includes subjecting the mutated population to radiation having a wavelength which can be absorbed by carotenoids. Such radiation causes chlorophyll in the microorganisms to fluoresce. Chlorophyll fluorescence levels are then monitored as an indication of the amount of chlorophyll in each microorganism. A mutated microorganism is then selected of having a chlorophyll fluorescence level above a predetermined level.

In another embodiment of the invention, photosynthetic microorganisms having increased cellular carotenoid content are selected by mutating a starting population of photosynthetic microorganisms. The mutated population is then cultured on a solid medium containing assimilable sources of carbon, nitrogen, inorganic nutrients, and an herbicide in the presence of light. Microorganisms having cellular carotenoid content Greater than the carotenoid content of the starting population have the ability to form colonies on the solid medium. The herbicides of this selection process can include carotenoid production inhibitors and oxygen radical generators.

Another embodiment of the present invention involves microorganisms selected by the above selection processes and in particular, microorganisms having a dry weight carotenoid content of at least about 0.8%. Such microorganisms can also have the characteristic of growing in tetrads. More particularly, the invention includes an alga of the species *Neospongioccum excentricum* having the identifying characteristic of ATCC Accession No. 40335 and mutations thereof.

A further embodiment of the invention includes a culture for the production of carotenoids by photosynthetic microorganisms, including microorganisms selected by the processes of the present invention.

A still further embodiment of the present invention includes a process for production of a carotenoid containing feed material by fermentation of photosynthetic microorganisms of the present invention. The process involves forming a culture including the photosynthetic microorganisms and assimilable sources of carbon, nitrogen, and inorganic elements. Fermentation conditions in the culture are regulated to promote cell growth. The microorganisms are then recovered from the fermented culture to form a feed material.

Another embodiment of the invention includes a process for the production of a carotenoid containing biomass by fermentation of microorganisms. A starting population of photosynthethic microorganisms is subjected to mutagenesis. A carotenoid overproducing microorganism is then selected from the mutated population, wherein the selected microorganism has an intracellular chlorophyll level greater than the level of said starting population. Alternatively, the microorganism can be selected for having resistance to an herbicide. A culture is formed from the progeny of the selected microorganism and assimilable sources of carbon, nitrogen, and trace nutrients. Growth conditions are maintained in the culture to promote growth of the microorganisms. The microorganisms are then recovered from the culture and a homogenized biomass is formed from the recovered microorganisms. An additional embodiment of the invention includes the carotenoid containing biomass produced by this process.

DETAILED DESCRIPTION

Figure 1:
FIG. 1 is an electron micrograph of strain B, ATCC Accession No. 40335, illustrating the tetrad cell configuration (magnification 26,000×).

The present invention is directed toward a method for selecting strains of photosynthetic microorganisms having high carotenoid content and microorganisms selected thereby. In particular, the selection method exploits a relationship between the chlorophyll content and the carotenoid content of the organism. While it has been known that carotenoids and chlorophyll are associated because both are involved in photosynthesis, it has now been determined that a direct correspondence exists between levels of carotenoids and of chlorophyll in *N. excentricum*. This relationship can be beneficially used for selecting microorganisms having high levels of carotenoids. This correspondence exists in wild type and most mutated strains. The correspondence, however, can be broken by mutation to produce, for example, a non-chlorophyll producing mutant having high carotenoid levels. One such mutant, strain A, is described in the Experimental section.

The selection process of the present invention using the relationship between the chlorophyll and carotenoid contents of photosynthetic microorganisms has been used to develop a division mutant strain of *N. excentricum* which grows in tetrads or conglomerates of tetrads at temperatures above about 25° C. and below about 38° C. The term "division mutant" refers to mutant strains having the phenotype of growing as multicellular aggregates rather than as unicellular organisms. No known references report division mutants in algae. Division mutants, however, have been recognized in yeast and bacteria.

The division mutant strain of the present invention is morphologically unique because it grows in tetrads and also because it has a high chloroplast to cell size ratio compared to unicellular algae of the same species. The division mutant strain of the present invention is particularly advantageous for carotenoid production because the high chloroplast to cell size ratio provides a high carotenoid content as a percentage of dry cell weight. Furthermore, the carotenoid content of the division mutant is stable with repeated culturing of the strain.

For the selection processes of the present invention, a starting population of photosynthetic microorganisms is mutated to induce genetic changes. Organisms undergoing beneficial mutations are then selected. The method of mutation employed in the selection methods of the present invention can be any of various chemical or physical mutation methods known in the art. For example, subjecting an organism to various concentrations of N-methyl-N'-nitro-N-nitrosoguanidine (NTG), ethylmethane sulfonate, hydrazine, or nitrous acid induces mutagenesis in microorganisms. A culture of microorganisms can also be mutated by subjecting the culture to physical mutagens, such as ultraviolet or gamma radiation.

With reference to the cell sorter selection method, carotenoids function as accessory pigments during photosynthesis and absorb light energy at a wavelength below that which can be absorbed by chlorophyll. The energy absorbed by carotenoids is transferred to chlorophyll, which then fluoresces red. This phenomena is used in the present invention by selecting microorganisms having high chlorophyll fluorescence levels when a culture of microorganisms is irradiated with light having a wavelength which is absorbed by carotenoids. Such microorganisms have correspondingly high carotenoid levels.

The cell sorter selection process is conducted by mutating a starting population of photosynthetic microorganisms. The mutated population is grown in a culture medium before the cell sorting process. The microorganism population is then exposed to light of a particular wavelength which is absorbed by carotenoids in the chloroplasts of the cells. This light energy is transferred to the chlorophyll and causes the chlorophyll to fluoresce red. A number of cells having increased levels of fluorescence are sorted and collected. These selected cells have increased levels of chlorophyll and correspondingly, have increased levels of carotenoids. If desired, these selected cells can be subjected to additional selection routines.

After mutagenesis of a culture of microorganisms in the manner described above, the organisms are allowed to grow prior to selecting improved mutants by cell sorting. This period of growth is necessary to allow organisms having the ability to produce high levels of intracellular carotenoids to grow and build up the carotenoid content of their cells. The length of this growth period depends upon the cell growth rate of the organism, as well as the medium composition and growth conditions, such as temperature. However, the growth period is usually at least about 8 hours long, more preferably, at least about 12 hours long, and most preferably at least about 24 hours long.

Microorganisms from the mutated culture having increased levels of carotenoids can be selected on the basis of chlorophyll fluorescence levels. As discussed above, carotenoids absorb light at a wavelength below that absorbed by chlorophyll and transfer the energy to chlorophyll which then fluoresces red. The carotenoid content of wild type *N. excentricum* has been found to be about eighty percent lutein and zeaxanthin in a ratio of about 9:1. Lutein and zeaxanthin absorb light having a wavelength between about 380 nanometers (nm) and about 500 nm. For cell sorting selection in accordance with the present invention, the mutated culture of microorganisms should be exposed to light having a wavelength within this range, and, more particularly, between about 415 nm and about 500 nm, and most particularly between about 440 nm and about 490 nm.

As a mutated culture of organisms is subjected to radiation, fluorescence levels of the chlorophyll present in the cells are monitored and organisms having increased levels of fluorescence are selected. Cells are selected on the basis of having fluorescence levels above a predetermined level. By setting a low predetermined level, a greater number of cells are selected and, conversely, a high predetermined fluorescence level results in selection of a smaller number of cells. The fluorescence level is determined according to the desired number of cells to be selected, which varies according to experimental design. For example, if the cell sorter selection is the final selection process before testing for carotenoid content, a smaller number of cells are selected because culturing and testing the carotenoid content of a large number of cells is difficult. However, if the cell sorter selection process is designed to be followed by an additional selection procedure, a much larger number of cells can be selected by a cell sorter because the number is later reduced by the additional selection procedure.

A desired fluorescence level is determined by selecting a cutoff point near the upper end of the range of fluorescence levels in the mutated population so that only a small number of cells are actually selected. Such a cutoff point is termed a "selection point". The distribution of fluorescence levels, indicating chlorophyll levels, in a population typically approximates a bell curve distribution. A large number of cells have average fluorescence levels, while fewer cells have either extreme high or extreme low levels of fluorescence. Cells having such extreme high and low levels of fluorescence are represented in a bell curve, respectively, by upper and lower tails of the curve. A selection point is selected so that cells in the upper tail of the curve are included. Typically, about 5.0% of the cells are selected, more preferably less than about 1.0% of the cells are selected, and most preferably only about 0.15% of the cells are selected.

A useful instrument for conducting a portion of the cell sorter selection process is a fluorescence activated cell sorter (FACS). Cell sorters of this type form a starting suspension of cells into droplets which are passed in front of a light source. The starting suspension is diluted to a concentration so that, on average, each droplet contains one cell. After the droplet is exposed to the light, the droplet is passed in front of a fluorescence sensor which detects the level of fluorescence from the cell. The FACS is calibrated so that fluorescence levels above a predetermined level are deflected into one container, while cells having a fluorescence level below the predetermined level are directed toward a separate container. In this manner, cells having a high fluorescence level are separated from the remaining cells in the suspension. A FACS can be used to determine the distribution of fluorescence levels prior to selection for purposes of determining a selection cutoff point.

In addition to separating cells on the basis of fluorescence, cells can also be fractionated on a size basis to prevent very large particles, such as clumps of cells, from being selected. The range of particle sizes which is selected for can be determined by finding the distribution of the particle sizes in the culture and selecting cutoff points to narrow the particle size range.

As mentioned above, the selected cells can be cultured to test for organisms having increased carotenoid content. Alternatively, the selected cells can be subjected to an additional selection procedure prior to testing for carotenoid content.

The division mutant strain of *N. excentricum* discussed above was developed, in part, with the cell sorter selection process and designated Strain B, ATCC Accession No. 40335. The strain identified by ATCC Accession No. 40335 has been deposited with the ATCC under the terms of the Budapest Treaty. Strain B has a high cartenoid content when measured as a percent of dry cell weight. It is believed that Strain B was selected by the cell sorter while in a tetrad configuration. Strain B was sorted as a mutant having a high chlorophyll content because four cells were processed in a tetrad by the cell sorter to cause a high fluorescence level, as compared with the remaining mutated organisms, which grow as unicellular organisms. Accordingly, the cell sorter selection process is useful for selecting division mutants of photosynthetic microorganisms.

A second selection method for selecting mutants having increased carotenoid content is to select photosynthetic microorganisms having increased chlorophyll levels on the basis of color rather than chlorophyll fluorescence. A mutated culture can be plated on a media suitable for growth and allowed to grow. As colonies form, colonies of microorganisms containing chlorophyll appear green. Colonies of microorganisms with increased levels of chlorophyll appear as a darker or more intense green. To select for high carotenoid content, the range of color of colonies is determined and the darkest or most intense green colonies are selected and tested. Typically, colonies in approximately the highest ten percent and, more preferably, in approximately the highest five percent of intensity are selected.

The relationship between chlorophyll and carotenoids discussed above is also the basis for selecting microorganisms which produce carotenoids in the presence of compounds which are carotenoid production inhibitors and oxygen radical generators. Such microorganisms are likely to be carotenoid overproducers. Carotenoids are believed to have a photoprotection function in addition to a photosynthetic function. During photosynthesis, oxygen radicals are generated by chlorophyll which can damage and kill cells. Without wishing to be bound by any particular theory, it is believed that carotenoids act as scavengers for oxygen radicals by reacting in some manner with the radicals to protect photosynthetic cells from damage. In unmutated photosynthetic cells, the level of carotenoids corresponds to the level of chlorophyll. Such corresponding levels of carotenoids are generally sufficient to protect cells from damage by oxygen radicals produced by chlorophyll. The present invention is directed toward selection methods for organisms having increased ability to produce carotenoids by subjecting a culture of mutated organisms to conditions which are lethal to organisms having a normal ability to produce carotenoids. A mutated culture of photosynthetic microorganisms is grown on a medium having a carotenoid production inhibitor or an oxygen radical generator. Under such conditions, organisms with a normal ability to produce carotenoids are unable to produce sufficient levels of these compounds to effectively function as photoprotecrive agents. Carotenoid overproducers, however, are able to produce sufficient levels of carotenoids, even in the presence of an inhibitor or an oxygen radical generator, to protect the cells from oxygen radicals generated during photosynthesis.

Many herbicides block carotenoid biosynthesis, and therefore, are lethal to photosynthetic microorganisms because there is no mechanism to protect organisms from oxygen radicals generated during photosynthesis. See Urbach, et al., *Effect of Substituted Pyridazinone Herbicides and of Difunone (EMD-IT 5914), on Carotenoids Biosynthesis in Green Algae*, 31 c Z. Naturforsch, pp. 652–55 (1976). By culturing photosynthetic microorganisms in the presence of a carotenoid production blocking herbicide and subjecting the microorganism to photosynthetic conditions, microorganisms having a normal ability to produce carotenoids are killed by the oxygen radicals generated during photosynthesis, while carotenoid overproducers can make sufficient amounts of carotenoids for protection from oxygen radicals.

Any herbicide or other composition having the effect of blocking or decreasing carotenoid production in photosynthetic microorganisms can be used in such selection methods. Such compositions include, but are not limited to Sandoz 9789 (4-chloro-5-(methylamino)-2-(3-(trifluoromethyl)phenyl)-3(2H)-pyridazinone; CAS Registry No. 27314-13-2), Difunone (5-((dimethylamino)methylene)-2,5-dihydro-2-oxo-4-phenyl-3-furan carbonitrile; CAS Registry No. 7703-36-8), Oxadiazon (3-[2,4-dichloro-5-(1-methylethoxy)-phenyl]-5-(1,1-dimethylethyl)-1,3,4-oxadiazol-2(3H)-one; CAS Registry No. 19666-30-9), Chloromequat chloride (2-chloro-N,N,N-trimethylethanaminium chloride; CAS Registry No. 999-81-5), 8-Hydroxyquinoline (8-Quinolinol; CAS Registry No. 148-24-3), and Bentazon (3-(1-methylethyl)-1H-2,1,3-benzothiadiazin-4(3H)-one 2,2-dioxide; CAS Registry No. 25057-89-0).

Other herbicides are known to function by increasing production of oxygen radicals during photosynthesis to a level at which carotenoids are unable to scavenge oxygen radicals to effectively protect cells from damage. In the presence of such compositions, carotenoid overproducers are able to generate sufficient amounts of carotenoids to protect cells better than microorganisms which produce less or normal amounts of carotenoids.

Any herbicide or other composition having the effect of Generating oxygen radicals during photosynthesis in photosynthetic microorganisms can be used in such selection methods. Such compositions include, but are not limited to viologens and in particular methyl viologen (1,1'Dimethyl-4,4'-bypyridinium; CAS Registry No. 4685-14-7) and benzyl viologen (1,1'-bis (phenylmethyl)-4,4'bypyridinium).

In addition to selection of high carotenoid producers by culturing mutated populations in the presence of herbicides which function either by blocking carotenoid production or by increasing oxygen radical generation, high carotenoid producers can be selected by culturing photosynthetic microorganisms in the presence of herbicides Generally. Any photosynthetic microorganism resistant to inhibition of Growth by herbicides, regardless of the mechanism of the herbicides, is likely to be an overproducer of carotenoids. By way of example, the herbicides oxyfluorfen (2-Chloro-1-(3-ethoxy-4-nitrophenoxy)-4-(trifluoromethyl) benzene; CAS Registry No. 42874-03-2) and fluometuron (N,N-Dimethyl-N'-[3-(trifluoromethyl)phenyl]urea; CAS Registry No. 2164-17-2) can be used to select for carotenoid over producers. All of the selection processes described above which involve the use of herbicides are preferred to, collectively, as "herbicide selection processes".

To select photosynthetic microorganisms having increased ability to produce carotenoids by herbicide selection processes, a culture of microorganisms is subjected to mutagenesis in the manner described above. The mutated culture is then plated on a growth medium containing the herbicide. For herbicide selection processes using carotenoid production inhibitors or oxygen radical generators to be effective, the mutated population must be subjected to light during growth. Otherwise, oxygen radicals are not generated by the photosynthetic process to kill cells having low levels of carotenoids. Viable colonies are then selected and carotenoid content is determined.

The concentration of herbicides in the selection process depends upon a number of factors, including the strength of the composition, the ability of the starting population to produce carotenoids, and the desired percentage of cells to be selected. While concentrations effective for selection can vary, a desired concentration of, for example, Sandoz 9789, is generally between about 1 uM and about 100 uM, more preferably between about 10 uM and about 90 uM, and most preferably between about 20 uM and about 70 uM.

The present invention is also directed toward strain B and other microorganisms produced by the selection methods described above. It will be apparent to one skilled in the art that in developing strains of microorganisms having high carotenoid content, a series of selection procedures can be conducted with gradual and continuous improvement in carotenoid yields. The series of selection procedures can involve repeating the same selection procedure or developing a strain through a series of different selection procedures.

Figure 2:
FIG. 2 is an electron micrograph of wild type *Neospongiococcum excentricum* (magnification 38,000×).

As discussed above and as described more fully in the Experimental Section, strain B was developed by both the cell sorter selection process and herbicide selection process. Strain B belongs to the species *Neospongiococcum excentricum* and has a green color. The alga is a division mutant and at temperatures of about 35° C. grows in tetrads with some formation of conglomerates of tetrads. At about 30° C., Strain B grows in tetrads without conglomerates and with some tetrads starting to fall apart into single cells. At temperatures of about 25° C. and below, only single cells are present. At about 38° C. and above, cell growth is decreased with mixed morphology of some single cells, some tetrads and some conglomerates of tetrads. FIG. 1 shows a thin section electron micrograph of Strain B, magnified by 26,000, in which the cellular structure of Strain B is apparent. Strain B has a high chloroplast to cell size ratio. It is believed that this characteristic is, at least partially, responsible for increased carotenoid production. A comparison of FIG. 1 with FIG. 2 showing the unicellular wild type illustrates the high chloroplast to cell size ratio of Strain B. The high chloroplast to cell size ratio is surprising because it is generally recognized that the chloroplasts of green algae are usually very constant in appearance within a single genus. See *Van Nostrand's Scientific Encyclopedia*, 80 (6th ed. 1983).

Cultures of Strain B can have carotenoid levels of between about 0.85% and about 1.1% cell dry weight when cultured on Medium A. (See Table 1) The carotenoid levels can generally be increased by about 0.1% to about 0.2% by culturing cells in the presence of light. The carotenoid content of a culture is determined by extracting carotenoids from a sample of the cell culture and determining the amount of carotenoids. This amount is divided by the total dry weight of cells from the same sized sample. The detailed procedure for carotenoid determination is provided in the Experimental section.

Strain B was developed from the wild type strain by a series of five selection steps. The first four steps involved herbicide selections, and the last was a cell sorter selection. The wild type is sensitive to 10 uM Sandoz 9789, while strain B is not sensitive to 100 uM Sandoz 9789, which is the limit of solubility in water. One of the prior mutant strains in the development of Strain B was selected for resistance to both Sandoz and benzyl viologen.

TABLE 1

| MEDIUM A | |
|---|---|
| $KH_2PO_4$ | 1.3 g |
| $K_2HPO_4$ | 9.2 g |
| $MgSO_4$ | 0.2 g |
| Trisodium citrate. $2H_2O$ | 10 g |
| $(NH_4)_2SO_4$ | 2.2 g |
| Carbon source: glucose or sucrose | 20 g |
| Trace Mineral Solution (see Table 2) | 10 ml |
| Urea | 5.0 g |
| Yeast Extract | 3.0 g |
| $H_2O$ (bring to volume) | 1.0 l |

[1]autoclave all components except for Trace Mineral Solution and urea.
[2]filter sterilize Trace Mineral Solution and urea.
[3]add Trace Mineral Solution and urea to remaining components.

TABLE 2

| TRACE MINERAL SOLUTION | | |
|---|---|---|
| | 200 ml (actual sol.) | Stock Conc. (g/l) |
| Distilled $H_2O$ | 20 ml | — |
| HCl | 2 ml | — |
| $CaCl_2.2H_2$ | 24 ml | 33.1 |
| $MnCl_2.4H_2$ | 20 ml | 1.4 |
| $ZnSO_4.7H_2$ | 20 ml | 8.82 |
| $CuSO_4.5H_2O$ | 20 ml | 1.57 |
| $COCl_2.6H_2O$ | 20 ml | 0.49 |
| $H_3BO_3$ (Boric Acid) | 20 ml | 11.4 |
| $Na_2MoO_4.2H_2O$ | 20 ml | 1.19 |
| Vanadyl Sulfate.$2H_2O$ | 10 ml | 2.0 |
| $NiN_O3.6H_2O$ | 2 ml | 1.0 |
| $CdSO_4$ | 2 ml | 1.0 |
| $FeSO_4.7H_2O$ | .25 g | — |
| $FeCl_3.5H_2O$ (make fresh every time) | 20 ml | 0.29 |

A problem encountered with the intermediate strains in the development to strain B was that initial high carotenoid levels became less in succeeding generations with repeated culturing. Strain B, however, has stable carotenoid levels of 0.85%–1.1% cell dry weight which do not deteriorate with repeated culturing.

In addition to having consistently high levels of carotenoids, the variation in carotenoid content of cultures of strain B is low. Twenty-four isolates of strain B (cultures of strain B derived from a single microorganism) were analyzed for carotenoid content. The values for carotenoid content only varied by about 0.15%. Variations in carotenoid content in isolates of the wild type strain and strain C (the development of strain C is discussed in the Examples section) of 0.35% to 0.40% were found. This characteristic of strain B, along with stable high carotenoid content, is favorable for commercial production of xanthophylls with strain B because consistent high yields are obtainable.

The carotenoid production by strain B and microorganisms selected by the processes described above can vary when different fermentation mediums and procedures are used. While many fermentation procedures are known by those in the art, a fermentation medium and process have been developed which produce consistently high growth rates and carotenoid production. The preferred fermentation medium for production of carotenoids by strain B is listed in Table 3.

TABLE 3

| Fermentation Medium | |
|---|---|
| | g/l |
| $KH_2PO_4$ | 3.88 |
| Sheftone E | 3.75 |
| $(NH_4)_2SO_4$ | 2.75 |
| $FeSO_4.7H_2O$ | 0.13 |
| Sterilize 90 minutes, 121° C. | |
| After sterilization, add: | |
| Glucose | 20.0 g/l |
| TM8 | 5.0 ml/l |
| $MgSO_4.7H_2O(1M)$ | 3.2 ml/l |

TABLE 4

| Trace Metal 8 (TM8) Solution | | |
|---|---|---|
| Component | | Stock Conc. (g/l) |
| HCl | 20 ml | — |
| $CaCl_2.2H_2O$ | 11.4 g | — |
| $MnSO_4$ | 50 ml | 24.6 |
| $CuSO_4.5H_2O$ | 2 ml | 15.7 |
| $COCl_2.6H_2O$ | 40 ml | 4.0 |
| Boric Acid | 40 ml | 22.8 |
| $ZnSO_4.7H_2O$ | 50 ml | 35.3 |
| $Na_2MoO_4.2H_2O$ | 40 ml | 1.2 |
| $VnSO_4.2H_2O$ | 40 ml | 2.0 |
| $Ni(NO_3)_2.6H_2O$ | 40 ml | 1.0 |
| $H_2O$ | up to 1 L | — |

Generally, the medium includes sources of carbon, nitrogen, phosphates, sulfates, magnesium, iron, and other trace metals. Glucose is the preferred carbon source in the present fermentation medium. While other carbon sources can support growth and production of carotenoids, it has been determined that glucose is more effective. The concentration of glucose in the fermentation medium should be maintained between about 5 g/l and about 30 g/l, more preferably between about 10 g/l and about 20 g/l, and most preferably between about 15 g/l and about 20 g/l. At glucose concentrations above these ranges, and particularly above about 40 g/l, a very sharp decrease in the growth rate of cells is observed and the rate remains at low levels until the level of glucose returns to below about 30 g/l as glucose is metabolized by the organisms.

It is preferable to initiate fermentation with a relatively high concentration of glucose which is within the given ranges so that growth is supported for a period of time before additions of glucose are required. The preferred ranges of glucose are maintained throughout the fermentation by adding additional amounts of glucose as levels are depleted by fermentation. Levels of glucose in the fermentation medium can be monitored by, for example, sampling the fermentation medium periodically and assaying for glucose concentrations. Alternatively, once a standard fermentation procedure is developed, additions of glucose can be made at timed intervals or at a predetermined rate corresponding to known levels of glucose at particular times throughout the fermentation. As will be recognized by those in the art, the rate of consumption of glucose and other nutrients increases during the fermentation as the cell density in the medium increases.

The fermentation medium also includes sources of nitrogen. In the preferred fermentation medium, a complex nitrogen source, Sheftone E, is provided. Sheftone E is a trademark for a complex nitrogen source product produced by the Sheffield Division of Kraft, Inc., which is a hydrolyzed mixture of animal and vegetable protein. Other complex nitrogen sources, such as Sheftone A, Sheftone F, N-Z Amine A-S or yeast extract, are suitable for use in the present fermentation medium. Optimal concentrations of these compositions can be determined by running test fermentations at varying concentrations of the complex nitrogen source while holding other variables constant and determining the highest carotenoid yield. It has been determined that Sheftone E should be present in a concentration of between about 2.0 g/l and about 4.0 g/l, more preferably between about 3.0 g/l and about 4.0 g/l, and most preferably between about 3.5 g/l and about 4.0 g/l. At concentrations at or above about 5 g/l, Sheftone E becomes inhibitory to strain B. At concentrations below about 2 g/l, no effect on growth or carotenogenesis is observed.

Nitrogen is also provided to the fermentation medium by addition of ammonium sulfate (($NH_4)_2SO_4$). At concentrations of ammonium sulfate below about 1.5 g/l, the ammonium is depleted by fermentation too quickly to support optimal growth. At concentrations of ammonium sulfate above about 5.0 g/l, the amount of sulfate added to the medium by ammonium sulfate, in addition to other sulfate sources, becomes inhibitory to growth. These values define the broadest range of ammonium sulfate concentrations, while ammonium sulfate is more preferably provided in amounts between about 2.0 and about 3.5 g/l and most particularly between about 2.5 g/l and about 3.0 g/l.

A final source of nitrogen to the fermentation medium is anhydrous ammonia gas or ammonium hydroxide which is added to the medium for purposes of controlling pH. As discussed below, the pH of the medium can be controlled by various means, but anhydrous ammonia gas is preferred because it provides an additional source of nitrogen.

Phosphates are provided in the fermentation medium by the addition of monobasic potassium phosphate ($KH_2PO_4$). This compound is initially provided to the fermentation medium at a concentration of between about 2.2 g/l and about 4.5 g/l, more preferably between about 2.5 g/l and about 4.0 g/l, and most preferably between about 3.5 g/l and about 4.0 g/l. These ranges of potassium phosphate provide phosphate to the medium at concentrations of between about 16 mM and about 33 mM. Throughout the fermentation, the phosphate concentration should be maintained within this range. At phosphate concentrations above about 33 mM and below about 16 mM, cell growth and carotenoid production is slowed. Throughout the fermentation, the concentration of phosphate should be maintained within this range. Such concentrations can be maintained with a number of phosphate sources known to those in the art, for example, phosphoric acid. Additionally, the initial phosphate concentration can be achieved with other sources of phosphate than monobasic potassium phosphate, such as dibasic potassium phosphate ($K_2HPO_4$) or sodium phosphate.

One source of sulfate in the preferred medium is ammonium sulfate. As discussed above, at concentrations above about 5.0 g/l, sulfate becomes inhibitory to cell growth, and at concentrations below about 1.5 g/l, the amount of sulfate provided by ammonium sulfate is too low to support sufficient cell growth. Accordingly, the initial concentration of ammonium sulfate in the fermentation is between about 15 mM and about 30 mM, and more preferably between about 19 mM and about 23 mM. Sulfates are also provided in the present medium by the addition of iron sulfate and magnesium sulfate which are discussed below. Alternative sources of sulfate in the present fermentation medium are acceptable if the sulfate is in a form which can be utilized by cells and which is non-toxic to cell growth.

Iron is provided to the fermentation medium by heptahydrate iron sulfate. The molar concentration of iron in the preferred medium is between about 0.270 mM and about 0.504 mM and more preferably between about 0.324 mM and about 0.468 mM. Concentrations of iron sulfate outside of these ranges effect a gradual decline in growth and productivity. Other sources of iron, such as ferric chloride, are suitable for use in the present fermentation medium.

Magnesium is provided to the fermentation medium by addition of heptahydrate magnesium sulfate. The starting concentration of this composition in the preferred fermentation medium is between about 2.0 mM and about 7.0 mM, more preferably between about 2.0 mM and about 5.5 mM, and most preferably between about 2.5 mM and about 5.5 mM. Other forms of magnesium are suitable for the present medium if the magnesium is in a form which can be utilized by cells for growth.

The preferred fermentation medium also contains a trace metal solution (Trace Metal 8 or TM8) containing the components listed in Table 4. The initial fermentation medium contains TM8 in concentrations of between about 2.5 ml/l and about 7.0 ml/l, and more preferably between about 3.5 ml/l and about 6.0 ml/l, and most preferably between about 4.0 ml/l and about 5.0 ml/l. Outside of these ranges, a gradual decrease in growth is observed. It should be recognized that other trace metal solutions can be used in accordance with the present invention provided that essential trace minerals are included. The primary components of the Trace Metal Solution, which are essential to successful growth, are copper, zinc, and calcium.

The preferred medium described above was specifically designed for fermentation of Strain B. However, it is believed that the medium is useful for fermentation of algae in the phyla Chlorophyta, more particularly for algae in the genus Neospongiococcum, and most particularly for the species *N. excentricum*.

In the development of strains of *N. excentricum* for production of carotenoids, it was observed that the species of algae has a slow growth rate. Additionally, it was recognized that for successful commercial production of carotenoids by fermentation of algae, high densities must be obtained. These two factors are important considerations in the fermentation procedure. It was recognized that to obtain acceptable cell densities in production tanks within 72 hours, that a two-stage inoculation is necessary to achieve a sufficiently high initial cell density. In the first stage, a culture of the algae is grown to a cell density of between about 6 g/l and about 7 g/l. This culture is then transferred to a seed tank and grown to a density of between about 30 g/l and about 40 g/l. The production tank is then inoculated with a 10% inoculum of this culture for the final fermentation to achieve an initial cell density of about 3 g/l to about 4 g/l. Using this procedure, a final cell density of between about 70 g/l and about 115 g/l can be obtained after 72 hours of fermentation. It should be noted that without the two-staged inoculation procedure, acceptable cell densities can be achieved by extending the fermentation time beyond 72 hours.

More particularly, to begin the inoculation procedure, a starting culture of the algae is provided. The starting culture can be, for example, a frozen subculture or a plated colony. It has been found that frozen subcultures are preferable and have higher initial growth rates than plated cultures. While not intending to be limited by theory, it is believed that frozen cultures have higher initial growth rates because they are frozen while in a growth phase, whereas plated cultures enter a stationary phase after forming colonies on a solid medium.

The starting culture is introduced to a shake flask containing an inoculum medium, similar to that described in the Experimental Section. This culture is grown, with agitation (375 RPM on a reciprocating shaker), for a time sufficient to achieve a cell density of between about 6 g/l and about 7 g/l. Typically, the shake flask culture achieves such cell densities between about 48 and 96 hours.

After a sufficient cell density has been achieved, the shake flask culture is transferred to a seed fermentor containing the fermentation medium described above. The seed fermentors are inoculated with 10% by volume inoculum and grown to a cell density of between about 30 g/l and about 40 g/l. Such cell densities are generally achieved in about 48 to 72 hours.

The seed culture is then transferred to a production fermentor as a 10% by volume inoculum to provide an initial cell density of between about 3 g/l and about 4 g/l. The fermentation medium initially contains the components described above in the ranges defined above. During the production fermentation, concentrations of some of the components can be monitored and additions of those components made when concentrations of the components fall below acceptable levels. The components which are monitored are sources of carbon, phosphate, sulfate, ammonia, iron, calcium and magnesium. As discussed above, levels of the various components can be determined by drawing samples and assaying for the component in question. Alternatively, the rate of depletion of various components can be determined by calculating the rate of depletion of a given component based upon the growth rate of the culture and the rate of utilization of the various components.

Throughout the fermentation, the temperature of the medium should be maintained between about 34° C. and about 36° C., more preferably between about 34.5° C. and about 35.5° C., and most preferably between about 34.9° C. and about 35.1° C.

The pH of the fermentation medium should be maintained between about 5.5 and about 6.5, and more preferably between about 5.8 and about 6.2. The pH of the medium can be regulated by various means known to those in the art. However, as discussed above, it is preferable to use anhydrous ammonia gas or ammonium hydroxide for pH control because the ammonia provides an additional source of nitrogen for the culture.

Dissolved oxygen in the fermentation medium must be maintained above levels to provide sufficient oxygen for utilization by the microorganisms. The dissolved oxygen content of the medium is preferably maintained above about 20% saturation and more preferably above about 30% saturation.

By using the microorganisms and fermentation processes discussed above, high cell densities of photosynthetic microorganisms having high carotenoid contents can be achieved. The carotenoids produced by such processes are most typically used as feed supplements in the form of a homogenized biomass. This product can be formed by separating cells from a finished fermentation broth. The cells are then broken apart to form a homogenized slurry. In this manner, the carotenoids are released into the slurry and made more available in the finished product. The slurry is then dried. For example, the slurry can be spray dried to form a feed product.

The following experimental results are provided for purposes of illustration and are not intended to limit the scope of the invention.

EXAMPLE I

Carotenoid Content of *Neospongiococcum excentricum*

A culture of wild type *Neospongiococcum excentricum* was obtained from the University of Texas at Austin Algal Culture Collection, Number 1232. A carotenoid content of cultures of wild type *N. excentricum* was determined for cultures grown under four sets of conditions. Under the first set of conditions, *N. excentricum* was cultured on Medium B with glucose in the dark. The composition of Medium B is listed in Table I-A. For the second set of conditions, the culture was grown on Medium B with glucose in the light. Under the third set of conditions, the culture was grown on Medium B with sucrose in the dark, and under the fourth set of conditions, the culture was grown on Medium B with sucrose in the light. For each of these cultures, the carotenoid content as a cell dry weight percent was determined in the manner described below.

TABLE I-A

| MEDIUM B | |
|---|---|
| $KH_2PO_4$ | 1.3 g |
| $K_2HPO_4$ | 9.2 g |
| $MgSO_4$ | 0.2 g |
| Trisodium citrate.$2H_2O$ | 1.0 g |
| $(NH_4)_2SO_4$ | 2.2 g |
| Carbon source: glucose or sucrose | 20 g |
| Trace mineral solution (see FIG. 4) | 10 ml |
| $H_2O$ (bring up to volume) | 1 L |

Trace mineral solution is not autoclavable, add as sterile solution after autoclaving.

A curve plotting absorbence against dry weight per ml was constructed by taking absorbence readings of cell suspensions at 600 nm and finding the cry weight per ml of each of the suspensions corresponding to an absorbence reading. The optical density readings taken to construct the curve where taken after diluting the suspensions by 1:100. A conversion factor of 0.1919 was determined from the curve.

To determine the dry weight per ml of samples 1–4, the sample was diluted 1:100 and the optical density (A600 nm) was taken. This reading was multiplied by one hundred and then by 0.1919 to obtain mg per ml. The results of this determination are shown in Table I-B.

TABLE I-B

| Sample No. | Optical Density A600 nm) | Dry Weight (mg/ml) |
|---|---|---|
| 1 | 0.541 | 10.38 |
| 2 | 0.332 | 6.37 |
| 3 | 0.247 | 4.74 |
| 4 | 0.327 | 6.28 |

To determine the carotenoid content of each of the samples, a carotenoid extraction was performed for each. For sample 1, 0.30 ml of the sample was pipeted into a test tube and 1.70 ml of dIH$_2$O water was added. For samples 2, 3 and 4, 0.50 ml of the sample was pipeted into a test tube and 1.50 ml of deionized water was added. Using a teflon-coated repipet, 5.0 ml of KOH saturated methanol was added to each sample. Using a glass repipet, 2.5 ml of hexane was added to each test tube. The test tubes were placed in a lab-Quake platform tube mixer and rotated for 30 minutes at room temperature. The tubes were removed from the mixer and 2.5 ml of dIH$_2$O was added to each tube. 2.5 ml of hexane was added to each tube with a repipet. The tubes were capped and rotated for an additional 30 minutes at room temperature. The tubes were removed from the mixer and allowed to separate for approximately 5 minutes. A spectrophotometer was set to 443 nm and blanked with a square cuvette containing hexane. The upper layer of each sample was removed with a Pasteur pipet and the OD (A443 nm) of each sample was determined, and is shown in Table I-C.

The carotenoid dry cell weight percent was determined using an extinction co-efficient for xanthophyll of 2350 (1%), in hexane at 443 nm to determine the dry weight per ml of carotenoids in each sample. The carotenoids as a percent of dry cell weight was determined by dividing the carotenoid weight by the total dry weight. The results of this determination are shown in Table I-C.

TABLE I-C

| Sample No. | Carotenoid Extraction (A443 nm) | Carotenoid (% Dry Cell Weight) |
|---|---|---|
| 1 | 0.335 | 0.290 |
| 2 | 0.560 | 0.374 |
| 3 | 0.404 | 0.363 |
| 4 | 0.633 | 0.428 |

The amounts of lutein and zeaxanthin in the carotenoids extracted from each of the cultures was determined by high-pressure liquid chromatography. The results of these tests are provided in Table I-D.

TABLE I-D

| Sample No. | Growth Condition | Hexane Extract* | Carotenoid Content HPLC L (% Dry Weight) | Z (% Dry Weight) | L + Z (% Dry Weight) | Z/(L + Z) (%) |
|---|---|---|---|---|---|---|
| 1 | Glucose, dark | 0.290 | 0.215 | 0.023 | 0.238 | 9.5 |
| 2 | Glucose, light | 0.374 | 0.393 | 0.014 | 0.407 | 3.4 |
| 3 | Sucrose, dark | 0.363 | 0.357 | 0.007 | 0.364 | 1.8 |
| 4 | Sucrose, light | 0.429 | 0.445 | 0.007 | 0.452 | 1.6 |

Sugars initially at 2%
*The hexane extract dry weight determinations were made by taking the total absorbance of the extract at 443 nm.

EXAMPLE II

Strain Selection

The wild type *N. excentricum* was subjected to mutagenesis by N-methyl-N'-nitro-N-nitrosoguanidine (NTG) according to the procedure outlined in Table II-A. 0.1 ml aliquots of the mutated cell suspension were plated on Medium B with 10 uM Sandoz 9789 with 2% glucose in the dark. Sixty-four mutant strains resistant to Sandoz 9789 were obtained with strain D having a dry weight carotenoid content of 0.4% as determined by the procedures discussed above.

TABLE II-A

N-METHYL-N'-NITRO-N-NITROSOGUANIDINE MUTAGENESIS PROCEDURE

1) Harvest cells by centrifuging 14 ml cells having an OD$_{600}$ of approximately 40, (approximately 5 × 10$^8$ cells ml).
2) Wash two times with about 7 ml 0.1M NaCitrate, pH 5.5, centrifuge.
3) Resuspend in 9.5 ml 0.1M NaCitrate (final volume, with cells, of about 10 ml); plate 1 ml @ 10$^{-7}$ to YMG 2% or YEP 2% (see Tables II-B and II-C) to count.
4) Add 50 ul of 5 mg/ml NTG in dimethyl sulfoxide (fresh) (final [NTG] 25 ug/ml); shake at 30° C. for 15 minutes.
5) Centrifuge.
6) Wash three times with 7 ml 0.1M NaH$_2$PO$_4$, pH 7.0, centrifuge.
7) Resuspend in 35 ml YMG 2% or YEP 2%, transfer to flask, grow at 30° C. dark for more than 3 hours.
8) Plate 0.1 ml of 10$^{-6}$ dilution on YMG 2% or YEP 2% to count survivors (expect about 25%).
9) Plate 0.1 ml on selective medium.

TABLE II-B

| YEP/AGAR | |
|---|---|
| | 1 L |
| Yeast extract | 3 g |
| Peptone | 5 g |
| H$_2$O | 900 ml |
| Agar | 20 g |

1. Combine above ingredients, add agar.
2. Autoclave at 121° C./15 psi.
3. Add 100 ml/L of carbon source before pouring.
4. Sterile glucose to 2% final concentration is added after autoclaving.

TABLE II-C

| YMG/Medium | |
|---|---|
| | 1 L |
| Yeast extract | 3 g |
| Malt extract | 3 g |
| Peptone | 5 g |
| H$_2$O | 900 ml |
| Agar | 20 g |

1. Combine above ingredients, add agar.
2. Autoclave at 121° C./15 psi.
3. Add 100 ml/L of carbon source before pouring.
4. Sterile glucose to 2% final concentration is added after autoclaving.

Strain D was subjected to ultraviolet (UV) mutagenesis according to the procedure outlined in Table II-D. 0.1 ml aliquots of the mutated cell suspension were plated on Medium B with 70 uM Sandoz 89 with 2% glucose in a lighted incubator. 77 mutant strains resistant to the Sandoz 9789 were obtained with mutant strain E having a dry weight carotenoid content of 0.76%. While Strain E was resistant to 70 uM Sandoz under lighted conditions, it was sensitive to 70 uM Sandoz in the dark.

TABLE II-D

ULTRA-VIOLET MUTAGENESIS PROCEDURE

1) Warm up lamp at least 1 hour (8 W, Sylvania germicidal Lamp "A").
2) Harvest 15 ml cells having an OD$_{600}$ of about 40.0 by centrifuging.
3) Wash twice with about 7 ml 0.1M Nacitrate, pH = 5.5, centrifuge.
4) Resuspend in 15 ml 0.1M Nacitrate, pH = 5.5.
5) Agitate 15 min. prior to irradiation with a stirbar.
6) Irradiate 1.5 to 7.0 min. (90% kill).

Strain E was plated to YMG medium containing 70 uM Sandoz. Plates were incubated in light and in dark. Four isolates resistant to 70 um Sandoz in the dark were obtained, and the mutant having the highest dry weight carotenoid content was strain F which had a carotenoid content of 1.15%. Carotenoid content in this mutant was unstable and gradually decreased to about 0.7-0.75% after repeated passages in the absence of Sandoz 9789.

Strain F was subjected to NTG mutagenesis as described in Table II-A. 0.1 ml aliquots of the mutated cell suspension were plated on YMG medium with glucose in the presence of 1 mM benzyl viologen and 70 uM Sandoz 9789 in limited light. Mutant strain C was selected having a dry weight carotenoid content of 1.10%. When cultured on Medium B with 1% urea, production of carotenoids with strain C was stimulated to 1.33%. Carotenoid production by strain C was examined in the presence of the following carotenoid-inhibiting herbicides: Difunone, Oxadiazon, Chlormequat chloride, and Bentazon, and none were found to specifically inhibit carotenogenesis. Carotenoid production, however, was unstable over time and with successive passages decreased from 1.10% to between 0.7% and 0.8%. Colonies of strain C are very dark green in appearance.

Single colony purification was performed with strain C cells. Individual colonies of strain C were spread on YEP medium with 70 uM Sandoz 9789. This procedure produced strain G which had an initial carotenoid content of 0.92%. This carotenoid level, however, deteriorated with time.

Figure 3:
FIG. 3 is an electron micrograph of strain H, illustrating its more highly developed lamellae system (magnification 38,000×).

Single colony purification was performed with strain G by spreading individual colonies on YEP medium in the presence of 70 uM Sandoz 9789. This procedure produced strain H having an initial carotenoid content of 1.17%. However, this level of carotenoid content decreased with time. Strain H has an intensely dark green color and has much more fully developed chloroplast lamellae system than wild type *N. excentricum* as seen in a comparison between FIGS. 2 and 3.

Figure 4:
FIG. 4 is an electron micrograph of strain A, illustrating its disorganized chloroplast (magnification 40,000×).

Strain H was subjected to NTG mutagenesis and plated on YEP medium in the presence of 50 uM oxyfluorfen with 2% glucose in the dark. This procedure yielded Strains A and I. These mutants had an initial carotenoid content of 1.3%, are gold in color, and light sensitive. Strain A had no organized chloroplast, but rather an amorphous mass as seen in FIG. 4.

Mutagenized organisms from the NTG mutagenesis of strain H were also plated on YEP medium with 15 uM fluometuron with 2% glucose in the light. Two mutants, Strains J and K, were obtained having an initial carotenoid content of 1.2%.

A second separate NTG mutagenesis of H was conducted and the mutants were plated on YEP medium with 100 uM oxyfluorfen. Mutant Strain L was produced having a 1.1% carotenoid content and a gold color.

Strain C was also subjected to NTG mutagenesis and the resulting mutant culture was grown for 3 days in Medium A at 30° C. This culture was diluted 1:100 in phosphate-buffered saline. Cells from the diluted culture were sorted with a fluorescence activated cell sorter on the basis of red fluorescence of the chlorophyll content of the cell when the cell is subjected to light of a particular wavelength. The cells were exposed to a 458 nm laser beam with a 515 nm cutoff filter, and cells activating fluorescence channels 165-229 were collected in 15 ml of phosphate-buffered saline. The highest 0.14% fluorescent medium sized particles (cells) (approximately 5000 cells) were collected, centrifuged, and suspended in 1 ml of phosphate-buffered saline solution. 0.1 ml samples of the suspension were plated on YEP medium containing 70 uM Sandoz 9789 with 2% glucose. Sandoz 9789 resistant mutant strain B was produced by this procedure. Strain B has a carotenoid content of 0.85-1.1%.

EXAMPLE III

Preparation of Frozen Subcultures

A 1.5 ml sample of a frozen stock of Strain B having a density of 6 g/l-7 g/l dry weight was introduced into a 4 liter baffled flask containing 400 ml of Medium A. The flask has baffles on the inner bottom surface. Near the bottom of the flask on the side is a serrated glass extension with silicon tubing attached. The flask also has an affixed high pressure liquid chromotography-type teflon septum which is located above the glass extension. The medium to flask volume was 1:10. Following inoculation, cells were propagated at 34°±1° C. in a reciprocating shaker for 96 hours at 375 rpm. At the end of this time period, dimethyl sulfoxide (DMSO) was added to the flask via the teflon septum to produce a 5% by volume concentration of DMSO in the medium. A sterile Cornwall syringe was aseptically connected to the affixed silicon tubing. Plastic cryo preservation vials were aseptically filled with 1.5 ml of cell suspension by repeated dispensing from the syringe. The filled vials were placed in a freezer at −70° C.

EXAMPLE IV

Preparation of Fermentor Inoculum

Fermentation inoculum medium was prepared according to Table IV-A. For this procedure, the Trace Metal 8 Solution was modified by adding $FeSO_4.7H_2O$ to a concentration of 21.6 mM. 400 ml of the medium was dispensed into a 4 liter flask and autoclaved for 35 minutes at 121° C.

TABLE IV-A

| Inoculum Medium | |
|---|---|
| | g/l |
| $KH_2PO_4$ | 3.10 |
| $(NH_4)_2SO_4$ | 2.20 |
| $MgSO_4.7H_2O$ | 0.62 |
| $FeSO_4 7H_2O$ | 0.10 |
| Sheftone E | 2.00 |
| Glucose | 20.0 |
| Bis-Tris | 12.60 |
| Trace Metal 8 (filter sterilized and added aseptically to autoclaved medium) | 4.0 ml/l |
| pH = 6.0 | |

A vial of frozen subculture was thawed at room temperature and mixed with a flask containing fermentation inoculum medium. The flask was incubated at 34°±1° C. for 96 hours in a gyrating shaker at 375 rpm.

Fermentation medium was prepared according to Table IV-B. Fourteen liter seed fermentors were sterilized at 125° C. for 45 minutes. The fermentors were cooled to 34° C.±1° C. Air flow was set to 1 vvm. The fermentors were agitated at 300 rpm. The pH in the medium was adjusted to 6.0 using anhydrous ammonia gas mixed into the air flow containing sterile air. The seed fermentor was inoculated with 800 ml of cell culture to 7200 ml of fermentation medium from the shake flask as a 10% by volume inoculum.

TABLE IV-B

| | Fermentation Medium | g/l |
|---|---|---|
| a. | KH₂SO₄ | 3.88 |
| b. | Sheftone E | 3.75 |
| c. | (NH₄)₂SO₄ | 2.75 |
| d. | FeSO₄.7H₂O | 0.13 |
| e. | Glucose | 20 |
| f. | Trace Metal 8 | 5 ml/L |
| g. | MgSO₄.7H₂O | 3.2 ml/L |

1. autoclave a–e for 90 minutes at 121° C.
2. add f and g.

Fermentation was conducted in the seed fermentor by maintaining temperature at 34° C.±1° C. The pH of the medium was maintained at 6.0±0.2 with anhydrous ammonia gas. Dissolved oxygen in the medium was maintained at greater than 30% saturation by controlling agitation. Glucose was maintained between 5 g/l and 20 g/l. Fermentation was continued for about 72 hours until a dry weight of 30–40 g/l was attained.

EXAMPLE V

Fermentation in Production Fermentor

Fermentation medium was prepared as described in Table IV-B. A 14 liter production fermentor was sterilized and cooled to 34° C.±1° C. Air flow was set to 1 vvm and agitation at 300 rpm. The pH was adjusted to 6.0 using anhydrous ammonia gas mixed with incoming sterile air. Inoculum from the seed fermentor was transferred to the production fermentor to produce a 10% by volume inoculum to provide an initial cell density of 3–4 g/l on a dry weight basis in a 10 liter final volume culture.

Fermentation was conducted at 34° C.±1° C. with pH maintained at 6.0±0.2 using anhydrous ammonia gas. Dissolved oxygen was maintained at greater than 30% saturation by control of agitation. Glucose was maintained at concentrations of between 5 g/l and 20 g/l.

Magnesium sulfate and Trace Metal 8 solution were also added to the fermentation medium during the process. The fermentation was stopped after 90 hours. A dry weight of 113 g/l with a carotenoid content of 0.81% was produced to give a final carotenoid yield of 915 mg of carotenoids per liter.

EXAMPLE VI

Fermentation in Production Fermentor

A fermentation was conducted as described in Example V, except that the fermentation ran for 48 hours. This process achieved a dry weight of 45 g/l with 0.85% carotenoids to yield 383 mg of carotenoids per liter.

EXAMPLE VII

Fermentation in Production Fermentor

A fermentation run was conducted as described in Example V, except that the initial inoculation in the production fermentor produced an initial cell density of 1–2 g/l on dry weight basis in a 10 liter final volume culture. The fermentation process was maintained for 96 hours to produce a final cell density of 70–80 g/l at 0.5%–0.6% carotenoids to yield 400–450 mg of carotenoids per liter.

EXAMPLE VIII

A series of 15 fermentation runs were conducted using strain B in 14 liter fermentation tanks. The medium for each of the runs was inoculation medium, as described in Table IV-A, except that Bis-Tris was not used as a buffer. The initial inoculation density for each fermentation was typically between about 3.0 g/l and about 4.0 g/l. The time for each of the fermentation runs and the results, including dry cell weight percent carotenoids, and total carotenoids, are provided in Table VIII-A.

As seen from the results in Table VIII-A, and particularly in the later runs, the dry cell weight is typically above 80 g/l, and in some cases above 110 g/l. The percent carotenoids are generally above 0.80% and in many cases above 0.90%.

TABLE VIII-A

| Fermentation Run Number | Time Hours | Dry Cell Weight (g/l) | Carotenoids (mg/l) | Percent Carotenoid % Dry Cell Weight |
|---|---|---|---|---|
| 1 | 89 | 6.0 | 42.4 | 0.86 |
| 2 | 109 | 26.1 | 214 | 0.82 |
| 3 | 185 | 66.1 | 560 | 0.85 |
| 4 | 47 | 57.1 | 554 | 0.97 |
| 5 | 70.5 | 87.0 | 605 | 0.70 |
| 6 | 47 | 50.5 | 424 | 0.84 |
| 7 | 51 | 79.1 | 617 | 0.85 |
| 8 | 56 | 81.5 | 791 | 0.97 |
| 9 | 68.5 | 84.6 | 613 | 0.72 |
| 10 | 57.5 | 97.5 | 864 | 0.89 |
| 11 | 57.5 | 112 | 916 | 0.81 |
| 12 | 57.5 | 119 | 872 | 0.73 |
| 13 | 69 | 88.8 | 854 | 0.94 |
| 14 | 60 | 87.6 | 827 | 0.93 |
| 15 | 60 | 85.5 | 788 | 0.92 |

EXAMPLE IX

A comparison between the ratio of carotenoid to chlorophyll levels in the wild type *Neospongioccum excentricum* and Strain C was conducted. The carotenoid content as a percentage of dry weight was determined by a standard assay taking the optical density of a carotenoid extraction. The chlorophyll content, as a percentage of dry weight, was determined by extraction with $CHCl_3:CH_3OH$ and calculated according to the equation of Arnon (concentration ug/ml=8.02 A663+20.2 A645). The results of this test are shown in Table IX-A. It can be seen from a comparison of the carotenoid to chlorophyll ratios of these two strains that a direct correspondence exists between the levels of carotenoids and chlorophyll.

TABLE IX-A

| Strain | Carotenoid % Dry Weight | Chlorophyll % Dry Weight | Carotenoid/ Chlorophyll |
|---|---|---|---|
| Wild Type | 0.392 | 2.14 | 0.183 |
| C | 0.845 | 4.67 | 0.181 |

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. An alga having the identifying characteristics of *Neospongiococcum excentricum* ATCC Accession No. 40335 and mutants thereof having said identifying characteristics, wherein said identifying characteristics comprise having a dry weight xanthophyll content of at least about 0.65% and being capable of growing to a cell density of greater than about 40 g/l.

2. A culture for the production of xanthophylls, said culture comprising:
   a) an alga having the identifying characteristics of *Neospongiococcum excentricum* ATCC 40335 and mutants thereof having said identifying characteristics, wherein said identifying characteristics comprising having a dry cell weight xanthophyll content of at least about 0.65% and being capable of growing to a cell density of greater than about 40 g/l;
   b) a carbon source in a concentration between 5 g/l and 30 g/l;
   c) a phosphate source having a molar concentration of phosphate of between 16 mM and 33 mM;
   d) a sulfate source having a molar concentration of sulfate of between 15 mM and 30 mM;
   e) an iron source having a molar concentration of iron of between 0.270 mM and 0.504 mM;
   f) a magnesium source having a molar concentration of magnesium of between 2.0 mM and 7.0 mM; and
   g) a source of nitrogen.

3. A culture as claimed in claim 2, wherein said carbon source comprises glucose, wherein said phosphate source comprises $KH_2PO_4$, wherein said sulfate source comprises $(NH_4)_2SO_4$, $MgSO_4.7H_2O$, and $FeSO_4.7H_2O$, wherein said magnesium source comprises $MgSO_4.7H_2O$, and wherein said iron source comprises $FeSO_4.7H_2O$.

4. A culture as claimed in claim 2, further comprising trace amounts of copper, calcium, and zinc, and wherein said nitrogen source comprises a complex nitrogen source.

* * * * *